US009655980B2

United States Patent
Bai et al.

(10) Patent No.: US 9,655,980 B2
(45) Date of Patent: May 23, 2017

(54) THERANOSTIC PLATFORM FOR TARGETED CANCER THERAPY AND DRUG DELIVERY MONITORING

(71) Applicants: Mingfeng Bai, Upper Saint Clair, PA (US); Pin Shao, Pittsburgh, PA (US)

(72) Inventors: Mingfeng Bai, Upper Saint Clair, PA (US); Pin Shao, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 967 days.

(21) Appl. No.: 13/955,944

(22) Filed: Jul. 31, 2013

(65) Prior Publication Data
US 2014/0037542 A1 Feb. 6, 2014

Related U.S. Application Data

(60) Provisional application No. 61/678,478, filed on Aug. 1, 2012, provisional application No. 61/683,067, filed on Aug. 14, 2012.

(51) Int. Cl.
*A61K 9/00* (2006.01)
*A61K 49/00* (2006.01)
(52) U.S. Cl.
CPC .......... *A61K 49/00* (2013.01); *A61K 49/0021* (2013.01); *A61K 49/0054* (2013.01)
(58) Field of Classification Search
CPC ...................................................... A61K 49/00
See application file for complete search history.

(56) References Cited

U.S. PATENT DOCUMENTS 6,124,458 A 9/2000 Muellen et al.

OTHER PUBLICATIONS

Ornelas et al, Combining Aminocyanine Dyes with Polyamide Dendrons: A Promising Strategy for Imaging in the Near-Infrared Region, Chem. Eur. J., 2011, 17, 3619-3629.*
Jiao et al, "Bis-N-annulated Quaterrylenebis(dicarboximide) as a New Soluble and Stable Near-Infrared Dye." *Org Lett.* 11(20):4508-4511.
Shao et al., "Photostable, hydrophilic and functional near infrared quarterrylenediimide-cored dendrimers for biomedical imaging," *Chem. Commu.*, 1(4); 2012.
Pschirer et al. "Pentarylene- and Hexarylenebis(dicarboximide)s: Near-Infrared-Absorbing Polyaromatic Dyes." *Angew. Chem. Int. Ed.*, 45:1401-1404, 2006.
(Continued)

*Primary Examiner* — Paul Dickinson
(74) *Attorney, Agent, or Firm* — Klarquist Sparkman, LLP

(57) ABSTRACT

A compound that includes a quaterrylene dye moiety as core, and a dendrimeric shell. For example, the compound may comprise at least four dendronized polyamides covalently attached to a quaterrylene dye. Also disclosed is a compound, or a pharmaceutically acceptable salt or ester thereof, comprising $A(G)_x$, wherein:
  A comprises a quaterrylene dye;
  G comprises at least one functionalized dendrimeric structure; and
  x is 2 to 16.
The compounds may be used for in methods for monitoring a therapeutic or diagnostic agent in a subject, or for treating a subject by administering the compound to the subject.

26 Claims, 2 Drawing Sheets

Structures of QR-G1-COOH and QR-G2-COOH.

(56) References Cited

OTHER PUBLICATIONS

Heek et al., "Highly fluorescent water-soluble polyglycerol-dendronized perylene bisimide dyes." *Chem. Commun.*, 46: 1884-1886, 2010.
Yukruk et al., "Water-Soluble Green Perylenediimide (PDI) Dyes as Potential Sensitizers for Photodynamic Therapy." *Org. Lett.* 7(14): 2885-2887, 2005.

\* cited by examiner

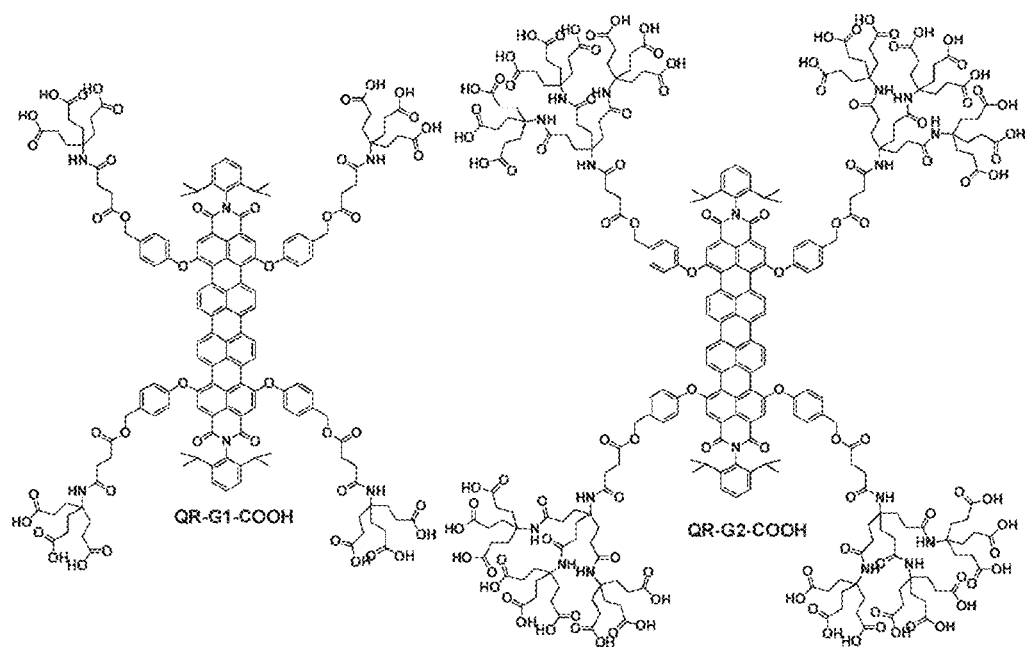
Fig. 1  Structures of QR-G1-COOH and QR-G2-COOH.
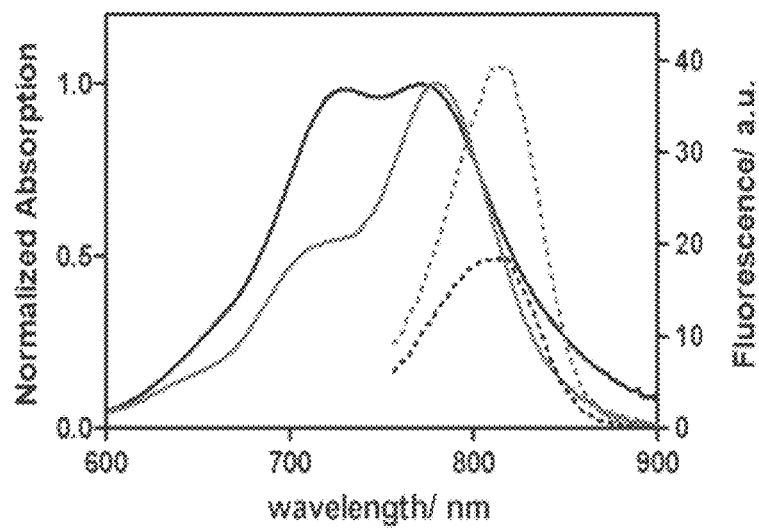
FIG. 2

THERANOSTIC PLATFORM FOR TARGETED CANCER THERAPY AND DRUG DELIVERY MONITORING

This application claims the benefit of U.S. Provisional Application No. 61/678,478, filed Aug. 1, 2012, and U.S. Provisional Patent Application No. 61/683,067, filed Aug. 14, 2012, both of which incorporated herein by reference in their entireties.

BACKGROUND

In general, current cancer therapy is inefficient. Cancer treatment relies heavily upon administration of cytotoxic drugs that attack both cancerous and healthy cells due to limited selectivity of drugs and widespread distribution of cytotoxic molecules throughout the body. The integration of targeted therapy and diagnosis has created a new genre in patient care and personalized medicine termed theranostics. Paramount to the success of this discipline is the ability to monitor targeted drug delivery using molecular imaging.

SUMMARY

Disclosed herein in one embodiment is a compound comprising a quaterrylene dye moiety as core, and a dendrimeric shell. For example, the compound may comprise at least four dendronized polyamides covalently attached to a quaterrylene dye.

Also disclosed herein is a compound comprising four dendronized polyamides covalently attached to a quaterrylene dye.

Disclosed herein in a further embodiment is a compound, or a pharmaceutically acceptable salt or ester thereof, comprising $A(G)_x$, wherein:
A comprises a quaterrylene dye;
G comprises at least one functionalized dendrimeric structure; and
x is 2 to 16.

Also disclosed herein is a method of monitoring a therapeutic or diagnostic agent in a subject, comprising administering to the subject a compound as described herein; and monitoring the compound within the subject.

Further disclosed herein is a method comprising administering to a subject a compound as described herein.

The foregoing will become more apparent from the following detailed description, which proceeds with reference to the accompanying figures.

BRIEF DESCRIPTION OF THE DRAWINGS

FIG. 1 shows the structural chemical formulae of two dendrimeric compounds disclosed herein.

FIG. 2 is a graph showing emission (dashed lines) and normalized absorption (solid lines) spectra of QR-G1-COOH (black) and QR-G2-COOH (red) at concentration of $1\times10^{-6}$ M in MeOH. $\lambda_{ex}$=720 nm.

DETAILED DESCRIPTION

Terminology

Figure 3:
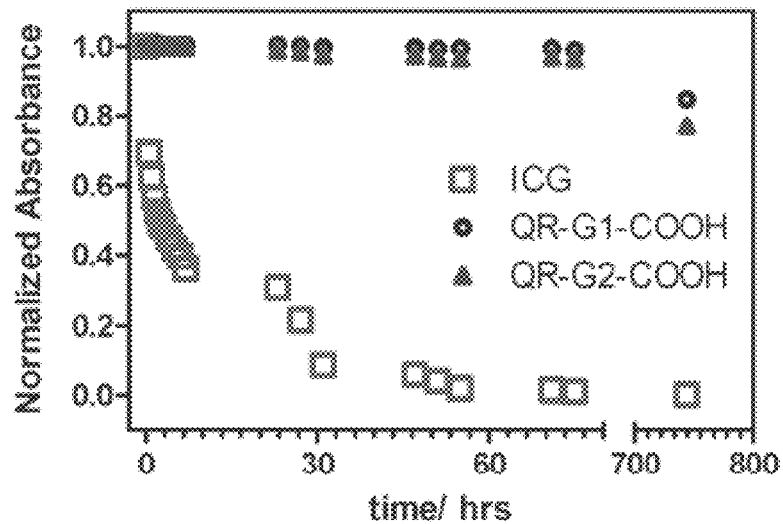
FIG. 3 is a graph showing the photostability of QR-G1-COOH, QR-G2-COOH and ICG in DMSO. Samples were exposed to the ambient light and the change of optical density at absorption maximum wavelength was monitored over time. All samples have the initial absorbance of about 1.2 at the absorption maximum wavelength. The signals were normalized against the values at 0 hour.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1\text{-}C_6)$alkyl can be methyl, ethyl, propyl, isopropyl, butyl, iso-butyl, sec-butyl, pentyl, 3-pentyl, or hexyl; $(C_3\text{-}C_6)$cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2, 2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The term "aralkyl" refers to an alkyl group wherein an aryl group is substituted for a hydrogen of the alkyl group. An example of an aralkyl group is a benzyl group.

"Aryloxy" or "heteroaryloxy" refers to a group of the formula —OAr, wherein Ar is an aryl group or a heteroaryl group, respectively.

The term "carboxylate" or "carboxyl" refers to the group —COO⁻ or —COOH.

The term "co-administration" or "co-administering" refers to administration of a dendrimeric compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by encapsulating the agents within the dendrimeric platform disclosed herein and/or by covalently conjugating the agents to the surface of the dendrimeric platform The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "hydroxyl" is represented by the formula —OH.

"Inhibiting" refers to inhibiting the full development of a disease or condition. "Inhibiting" also refers to any quantitative or qualitative reduction in biological activity or binding, relative to a control.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. For example, a therapeutically amount may be an amount of a FBXO3 inhibitor that is sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits inflammation in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Overview

Current theranostic agents are usually nanoparticle based, which allows for incorporation of multiple drug and imaging molecules. Dendrimers provide a superior theranostic platform compared to other nanoparticles due to their precisely controlled size, shape, and surface chemistry. These unique properties allow dendrimers to be developed with high structural monodispersity, desired plasma circulation time and biodistribution properties, as well as control over drug release. In addition, targeting and signaling moieties can be attached to the surface functional groups of dendrimers to allow targeted drug delivery and therapeutic monitoring. Disclosed herein is a novel dendrimer platform that is superior to existing technology and has the potential to be widely applied to cancer therapy and monitoring.

As a low-cost and highly sensitive imaging modality, optical imaging is widely used in cancer diagnosis, therapeutic monitoring and intraoperative guidance. For in vivo imaging, near infrared (NIR) fluorescent dyes are usually used as the fluorophores because of the relatively deep tissue penetration and negligible autofluorescence in the NIR region. When adapted as part of theranostic dendrimers, NIR dyes are typically conjugated to the surface of dendrimers. This approach, however, has two limitations: (1) most NIR dyes used in biomedical imaging are polymethine cyanine dyes that are unstable and prone to photobleaching; (2) polymethine cyanine dyes often self-quench due to the small stoke shift, resulting in poor fluorescence signal. To overcome these limitations, disclosed herein is an innovative theranostic dendrimer platform with a core composed of a novel highly photostable, fluorescent and chemically stable NIR fluorescent dye. This theranostic dendrimer platform has desired maximum absorption and emission wavelengths in the center of the NIR region. A photostability study demonstrated that the presently disclosed theranostic dendrimer platform is dramatically more stable than FDA approved NIR fluorescent dye, indocyanine green (ICG). Such an innovative platform will allow for longer imaging time, higher fluorescence signal and more accurate quantification. It is noteworthy that this dendrimer platform is not limited to optical imaging applications. For example, it is possible to use this technology in positron emission tomography (PET), single-photo emission computed tomography (SPECT) or magnetic resonance imaging (MRI) by attaching chelated $^{64}Cu^{2+}$, $^{111}In^{3+}$ or $Gd^{3+}$ to the dendrimer surface. Therefore, these compounds will find wide applications in cancer therapy.

Disclosed herein is the first functional quaterrylene dye and quaterrylene-based NIR fluorescent theranostic dendrimer platform. This innovative dendrimer platform outperforms the existing NIR theranostic dendrimers with extremely high chemical stability, photostability and fluorescence. Such design avoids self-quenching and photobleaching problems of the current technology, and leave all the surface functional groups available for conjugation of drugs and targeting molecules. As a result, this transformative technology will have high fluorescence intensity and allow for long-term non-invasive therapeutic monitoring in a wide range of cancers. It will be possible to conjugate various targeting molecules, signaling moieties and drugs to this innovative platform and thereby have the potential to transform the way that cancer patients are treated and monitored. In addition, the capability of NIR fluorescence imaging will provide opportunities for intraoperative guidance.

Disclosed herein is the first photostable near infrared (NIR) theranostic dendrimer platform, which is based on a novel functional quaterrylene dye as the dendrimer core. Such innovative design avoids the photobleaching and self-quenching issues of current NIR dendrimers, thus allowing NIR theranostic studies with longer imaging time, higher fluorescence signal and more accurate quantification. In addition, all the surface functional groups will be available for conjugation to drugs and targeting molecules. In one example, the quaterrylene-based theranostic dendrimer platform compounds have absorption at around 790 nm and emission at around 830 nm, in the most preferred NIR region for in vivo optical imaging. The photostability study showed that the NIR theranostic dendrimer platform compounds have orders of magnitude higher photostability than FDA approved NIR fluorescent dye, ICG. In addition, cytotoxicity and cell imaging studies demonstrated that this photostable NIR theranostic dendrimer platform was highly biocompatible. These results indicate that this theranostic platform has great potential to be widely applied in cancer research.

Described herein is a new class of near infrared (NIR) fluorescent dendrimeric quaterrylenediimide dyes with high photostability and hydrophilicity, functionality, as well as low cytotoxicity. There has been considerable effort in the development of near infrared (NIR, 700-900 nm) fluorescent dyes for in vivo optical imaging, due to the relatively deep tissue penetration and negligible autofluorescence in the NIR region. Ideally, an optimal NIR fluorescent dye used for biomedical imaging has the following merits: (1) possessing high molar extinction coefficient (absorbance) and quantum yield (fluorescence); (2) having high chemical and photophysical stability; (3) being biocompatible (low cytotoxicity); (4) showing hydrophilicity (water solubility); and (5) containing functional groups for bioconjugation to targeting moieties such as antibodies, proteins, peptides, receptor ligands and carbohydrates. Unfortunately, few NIR dyes have all the desired properties. Typical NIR dyes are of the polymethine cyanine dye family, comprising benzoxazole, benzothiazole, indolyl, 2-quinoline and 4-quinoline subclasses. These dyes have adjustable optical properties and high extinction coefficients (>150 000 $M^{-1}$ $cm^{-1}$). In addition, many cyanine dyes can be easily conjugated to targeting moieties, imparting molecular specificity to targeted cells or tissues. Unfortunately, conventional NIR cyanine dyes suffer from some limitations. Most of these dyes decompose over time under ambient conditions and are readily photobleached under intense illumination. Therefore, there is a need to develop novel NIR dyes to improve chemical stability and photostability.

Quaterrylene dyes were recently developed for solar cells to conduct solar energy. Although these quaterrylene dyes are not suitable for biomedical imaging due to poor hydrophilicity and no functionality, they exhibit extremely high molar extinction coefficients (>150 000 $M^{-1}$ $cm^{-1}$), outstanding quantum yields (>0.55), as well as excellent chemical and photostability. In addition, this class of dyes has absorption and emission wavelength close to 800 nm, the most preferred wavelength for NIR fluorescence imaging. These properties make quaterrylene dyes stand out as very attractive fluorescent imaging dyes; however, no quaterrylene dyes suitable for biomedical imaging have been developed. One of the largest obstacles is aggregation, which is a common issue of dyes with large and rigid p-electron systems, such as quaterrylene dyes. To circumvent this challenge and take advantage of the outstanding spectroscopic properties of quaterrylene dyes, disclosed herein is a dendrimeric platform compound with four dendronized polyamides covalently attached to the bay regions of a new quaterrylene dye. Polyamide dendrimers can enhance the biocompatibility of materials and have been used to improve dye properties. Such a design will also increase hydrophilicity and introduce functionality. To demonstrate the concept, disclosed herein are the first two generations of this new quaterrylene-dye based dendrimer family, QR-G1-COOH and QR-G2-COOH (see FIG. 1).

For example, disclosed herein are two polyamide-based quaterrylenediimide dendrimers (QR-G1-COOH and QR-G2-COOH) with twelve and thirty-six carboxylic acid groups, respectively. With strong NIR absorption, remarkable photostability, low toxicity to DBT cells, high hydrophilicity and functionality ready for bioconjugation, these NIR dendrimers are promising for biomedical imaging applications. In addition, QR-G2-COOH appears to be more emissive than QR-G1-COOH, indicating that increasing dendrimer size is an effective strategy to improve the emission of the quaterrylenediimide dendrimers.

Compounds

Disclosed herein in one embodiment are compounds that can be used as theranostic platforms that include a quaterrylene dye moiety as core, and a dendrimeric shell.

The dendrimeric shell is a three-dimensional supramolecular radial symmetrical structures comprising an initiator node, such as nitrogen, an amine such as ethylenediamine or propylamine, with interior layers attached to the dye core which are comprised of, for example, three or four arms with each arm being composed of repeating units, and with the number of repeating units in each arm considered to be a generation of the dendrimer. The outermost generation typically contains terminal functional groups, such as a primary amine, an ester, a carboxylate, or a carboxylic acid attached to the outermost generation. The size and shape of the dendrimeric shell, and the functional groups present therein can be controlled by the choice of the initiator node, the number of generations, and the nature of the repeating units employed at each generation. For example, the chemical functionality of the repeating units in the interior layers can be, amidoamines, such as diethylene diimine, and with terminal functionalities, such as, for example, amino groups, hydroxyl groups, carboxylic acid groups, carboxylates and the like. Therefore, dendrimeric shells are combinations of monomeric units which allow branching at each step of polymerization. Dendrimeric shells tend to form globular structures with increasing numbers of monomeric units, which eventually will cover the dye core.

For example, disclosed herein is a compound that includes at least one quaterrylene dye core moiety covalently attached to at least four dendronized polyamides. Other dendrimeric structures could be used such, for example, polyamidoamine (PAMAM), polypropylenimine, phosphorus, and/or polylysine dendrimeric structures, provided these structures include functional groups for bioconjugation to the quaterrylene dye core moiety. In certain embodiments, there are four, eight, twelve, or sixteen dendronized polyamide arms covalently attached to a single quaterrylene dye core moiety. The dendronized polyamides may be functionalized, for example, with a carboxylate, carboxylic acid or anhydride thereof, hydroxyl, amino, azide, alkynyl, activated alkene (such as maleimide), thiol, thioether, thioester, haloacetamide, disulfide, aldehyde, hydrazide, alkoxyamine, hydrozone, thiocyanate, isothiocyanate, cyanate, isocyanate, or squarate functional group(s). In certain embodiments, the dendrimeric compounds disclosed herein may also include at least one moiety, selected from a therapeutic moiety, a targeting moiety, a signaling moiety, a hydrophilic moiety, or a combination thereof, that are conjugated to the dendrimeric compounds via the functional groups (e.g., carboxylate or carboxylic acid) of the functionalized dendronized polyamides. For example, the dendronized polyamides may be functionalized so that they are activated for conjugation with the other moieties (e.g., a therapeutic moiety, a targeting moiety, a signaling moiety, a hydrophilic moiety, or a combination thereof). For instance, the compound may be functionalized with a dicarboxylic acid or anhydride (e.g., succinic, glutaric, citraconic or adipic) to provide appropriate reactive groups (e.g., amine, carboxyl or hydroxyl terminal groups). In certain embodiments, the moiety may be conjugated to the dendrimeric shell via an ester or amide linkage. In certain embodiments, a therapeutic agent or moiety, a targeting agent or moiety, a signaling agent or moiety, or a combination thereof may be encapsulated within the dendrimeric platform.

In certain embodiments the functionalized dendronized polyamides include an ester- or polyester-containing linkage between the quaterrylene dye core moiety and the amide. The carbon atom adjacent the nitrogen atom of the amide may be a branch point for a plurality of ester- or polyester-containing dendritic branches that may be functionalized with the functional groups described above.

The quaterrylene dye core moiety may be any structure that exhibits the desired absorption and admission properties, typically within the NIR. Illustrative quaterrylene dye core moieties include those disclosed, for example, in U.S. Pat. No. 6,124,458, which is incorporated herein by reference in its entirety. In certain embodiments, the quaterrylene dye core moiety is derived from a 1,6,11,16-tetraaryloxy-quaterrylene-3,4:13,14-tetracaroxylic diimide having a structure of:

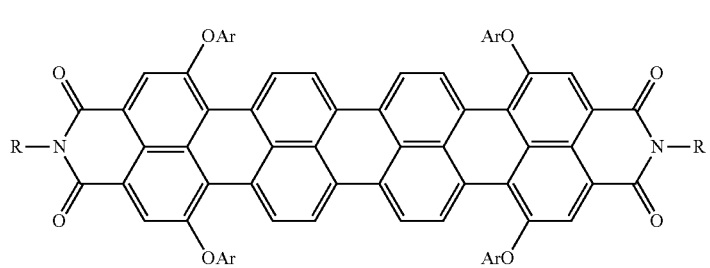

Formula I wherein R is hydrogen; $C_1$-$C_{30}$-alkyl whose carbon chain may be interrupted by one or more of —O—, —S—, —NR$^1$—, —CO— and/or —SO$_2$— and which may be monosubstituted or polysubstituted by cyano, $C_1$-$C_6$-alkoxy or a 5-, 6- or 7-membered heterocyclic radical which is attached via a nitrogen atom and which may contain further heteroatoms and may be aromatic, where R$^1$ is hydrogen or $C_1$-$C_6$-alkyl; $C_5$-$C_8$-cycloalkyl whose carbon skeleton may be interrupted by one or more of —O—, —S— and/or —NR$^1$—; aryl or heteroaryl, which may each be monosubstituted or poly-substituted by $C_1$-$C_{18}$-alkyl, $C_1$-$C_6$-alkoxy, cyano, —CONHR$^2$, —NHCOR$^2$ and/or aryl- or heteroarylazo, which may each be substituted by $C_1$-$C_{10}$-alkyl, $C_1$-$C_6$-alkoxy or halogen, where R$^2$ is hydrogen; $C_1$-$C_{18}$-alkyl; aryloxy, arylthio, heteroaryloxy or heteroarylthio, which may each be substituted by $C_1$-$C_4$-alkyl or $C_1$-$C_4$-alkoxy; and Ar is a substituted aryl group.

In certain embodiments, R of the quaterrylene dye core moiety precursor of Formula I is an aryl, particularly a phenyl, that is substituted with a $C_1$-$C_{18}$ alkyl, particularly meta-di-substituted, especially with isopropyl. In certain embodiments, Ar is a para-substituted phenyl, particularly with a carbonyl (e.g., —C(O)H) or a carboxylic acid (e.g., —C(O)OH).

Chains that may be dendrimerized (the dendrimerized chain is referred to herein as a "dendron chain") and optionally further functionalized may be covalently attached to the quaterrylene dye core moiety at any suitable position. For example, with a quaterrylene dye core moiety precursor of Formula I, the chains may be covalently attached to the quaterrylene dye core moiety at the 1,6,11,16-tetraaryloxy positions. For example, an intermediate compound may be made wherein each dendron chain includes an ester and an amide linkage, wherein the amide linkage is the attachment point for 1, 2 or 3 ester chains (see, e.g., the triester compounds 9 and 10 disclosed in Scheme 1).

Each dendron chain may be end-functionalized with, for example, carboxylic acid or anhydride thereof, carboxylate, hydroxyl, amino, azide, alkynyl, activated alkene (such as maleimide), thiol, thioether, thioester, haloacetamide, disulfide, aldehyde, hydrazide, alkoxyamine, hydrozone, thiocyanate, isothiocyanate, cyanate, isocyanate, squarate, or a combination thereof. Each dendron chain may be functionalized so that they are activated for conjugation with the other moieties (e.g., a therapeutic moiety, a targeting moiety, a signaling moiety, a hydrophilic moiety, or a combination thereof). For instance, the compound may be functionalized with a dicarboxylic acid or anhydride (e.g., succinic, glutaric, citraconic or adipic) to provide appropriate reactive groups (e.g., amine, carboxyl or hydroxyl terminal groups).

In certain embodiments, a first quantity of dendron chains are functionalized, for example, with a first functional group such as a carboxylate or a carboxylic acid, a second quantity of dendron chains are functionalized, for example, with a second different functional group such as a signaling moiety, and optionally further quantities of dendron chains are functionalized with further different functional groups. In certain embodiments the compounds include at least four, more particularly at least eight, and most particularly at least twelve, dendron end-functional groups. For example, the compound may include 4, 12, 36, 108, etc., functional groups.

Illustrative therapeutic moieties include anti-cancer agents, anti-inflammatory agents, anti-bacterial agents, antiviral agents, cognitive function modulators, vascular function modulators, and the like. In certain embodiments, the therapeutic moiety is an anti-cancer agent. Specific examples include methotrexate, doxorubicin, paclitaxel, 5-fluorouracil, camptothecin, cisplatin, carboplatin, oxaliplatin, DACH-Pt, melphalan, chlorambucil, thiotepa, busulfan, etoposide, vinblastine, podophyllotoxin, colchicine, taxol, hydroxyurea, and 5-azacytidine.

Illustrative signaling moieties include radioisotopes (such as $^{18}$F, $^{11}$C, $^{64}$Cu$^{2+}$ and $^{111}$In$^{3+}$) for PET and SPECT, supermagnetic (such as iron oxide) or paramagnetic (such as gadolinium) metals for MRI, fluorophores (such as dyes, quantum dots and nanoparticles) for optical and/or photoacoustic imaging, microbubbles for ultrasound and iodine for CT.

Illustrative targeting moieties include receptor ligands, peptides, proteins, antibodies, antibody fragments and nucleic acids. The targeting moiety assists in selectively directing the compound to a desired target such as cancer tissue.

The hydrophilic moiety may be any group that can solubilize the compound in an aqueous environment. The hydrophilic moiety can include an ionic or non-ionic group. Examples of anionic groups include $SO_3^{-2}$, $COO^{-1}$, $PO_4^{-3}$, and the like. Examples of cationic groups include $(CH_3)_3N^{+1}$, $(CH_3CH_2)_3N^{+1}$, $(HOCH_2CH_2)_3N^{+1}$, methyl pyridine$^{+1}$, multivalent cationic groups, and the like. Amphoteric groups that include both anionic and cationic groups in the same moiety may also be utilized. Examples of non-ionic groups include polyalkylene oxides (e.g., polyethylene glycol (PEG)), polyglycerol, poly(vinyl alcohol), mono, oligo and polysaccharides and their derivatives, and the like. The hydrophilic moiety, particularly a hydrophilic polymer, may a certain molecular weight range. In the case of PEG, a MW of 300 to 20,000, more particularly 1,000 to 10,000, and most particularly 2,000 to 10,000, may be preferred.

A further embodiment disclosed herein is a compound, or a pharmaceutically acceptable salt or ester thereof, comprising A(G)$_x$, wherein:

A comprises a quaterrylene dye;

G comprises at least one functionalized dendrimeric structure; and x is 2 to 16.

The quaterrylene dye A may be a quaterrylene dye moiety as described above, and the dendrimeric structure G may be covalently bonded to A at the positions as described above. In certain embodiments, x is 4.

The functionalized dendrimeric structure G may include a branched ester, a branched amidoester, a branched alkyl carboxylate or a branched alkyl carboxylic acid structure. In certain embodiments, the dendrimeric structure G includes a structure of:

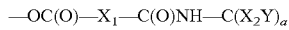

—OC(O)—X$_1$—C(O)NH—C(X$_2$Y)$_a$ wherein X$_1$ and X$_2$ are each individually an alkanediyl, particularly $C_1$-$C_6$ alkanediyl, or X$_2$ is —X$_1$—C(O)NH—C(X$_2$Y)$_a$;

Y is a functional group selected from carboxylic acid or an anhydride thereof, carboxylate, hydroxyl, amino, azide, alkynyl, activated alkene (such as maleimide), thiol, thioether, thioester, haloacetamide, disulfide, aldehyde, hydrazide, alkoxyamine, hydrozone, thiocyanate, isothiocyanate, cyanate, isocyanate, squarate, or a combination thereof; and a is 1 to 3, more particularly 3.

There may be any number of generations of the dendrimeric structure G or dendrimer shell, such as generation 0, generation 1, generation 2, generation 3, generation 4, generation 5, etc. For example, QR-G1-COOH represents a first generation dendrimeric structure G, and QR-G2-COOH represents a second generation dendrimeric structure.

In certain embodiments, Y is a functional group that may be activated for conjugation with the other moieties (e.g., a therapeutic moiety, a targeting moiety, a signaling moiety, a hydrophilic moiety, or a combination thereof). For instance, Y may include a dicarboxylic acid or anhydride (e.g., succinic, glutaric, citraconic or adipic) to provide appropriate reactive groups (e.g., amine, carboxyl or hydroxyl terminal groups). In certain embodiments, the compound includes a targeting moiety and a therapeutic moiety. In certain embodiments, the compound includes a targeting moiety and a signaling moiety.

In certain embodiments, the compounds may have an absorption wavelength of 500 to 1100, more particularly 600 to 950, and most particularly 700 to 850, nm. In certain embodiments, the compounds may have an emission wavelength of 520 to 1120, more particularly 620 to 970, most particularly 720 to 870, nm.

In certain embodiments, the compounds disclosed herein are dramatically more photostable than FDA approved NIR fluorescent dye, indocyanine green (ICG). As shown in FIG. 3, after being exposed to ambient light for only 2 hours, the absorbance of ICG solution decreased by 48%, whereas solutions of QR-G1-COOH and QR-G2-COOH exhibited no significant absorbance change. After 3 days of illumination, no significant absorbance from ICG sample was observed, while QR-G1-COOH and QR-G2-COOH showed an absorbance change of only 1% and 3%, respectively. Even after being exposed to the ambient light for 31 days, QR-G1-COOH and QR-G2-COOH remained strong NIR absorbance of 85% and 77%, respectively.

The diameters of G1-G5 quaterrylenediimide-based dendrimers are approximately 2 nm, 3 nm, 4 nm, 6 nm and 8 nm respectively.

The compounds disclosed herein may also be used for positron emission tomography (PET), single-photo emission computed tomography (SPECT), magnetic resonance imaging (MRI), optical imaging, photoacoustic imaging, ultrasound and computed tomography (CT) by attaching radioisotopes (such as $^{18}F$, $^{11}C$, $^{64}Cu^{2+}$ and $^{111}In^{3+}$) for PET and SPECT, supermagnetic (such as iron oxide) or paramagnetic (such as gadolinium) metals for MRI, fluorophores (such as dyes, quantum dots and nanoparticles) for optical and/or photoacoustic imaging, microbubbles for ultrasound and iodine for CT.

Pharmaceutical Compositions

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, another anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Scheme 1 (below) outlines a synthetic strategy towards developing QR-G1-COOH and QR-G2-COOH. In order to synthesize the important precursor of quaterrylene, biperylene compound 6, two approaches were used—Yamamoto coupling and Suzuki coupling. Yamamoto homocoupling with bis(cycloocta-1,5-diene)nickel(0) [Ni(COD)2] has been used to synthesize some biperylenes; unfortunately, it afforded the biperylene 6 with rather low yield (14%). To improve this reaction yield, the Suzuki coupling of 9-bromoperylenedicarboximide 4 and its boronic ester 5 was attempted. Although this approach requires an additional step to synthesize 5, biperylene 6 was found as a by-product during the synthesis of the boronic ester 5, and the overall conversion yield from 4 to 6 was greatly improved (from 14% to 62%). In addition, toxic Ni(COD)$_2$ is avoided by using a Pd catalyst. Therefore, Suzuki coupling appears to be a much better method for the synthesis of 6 than Yamamoto coupling.

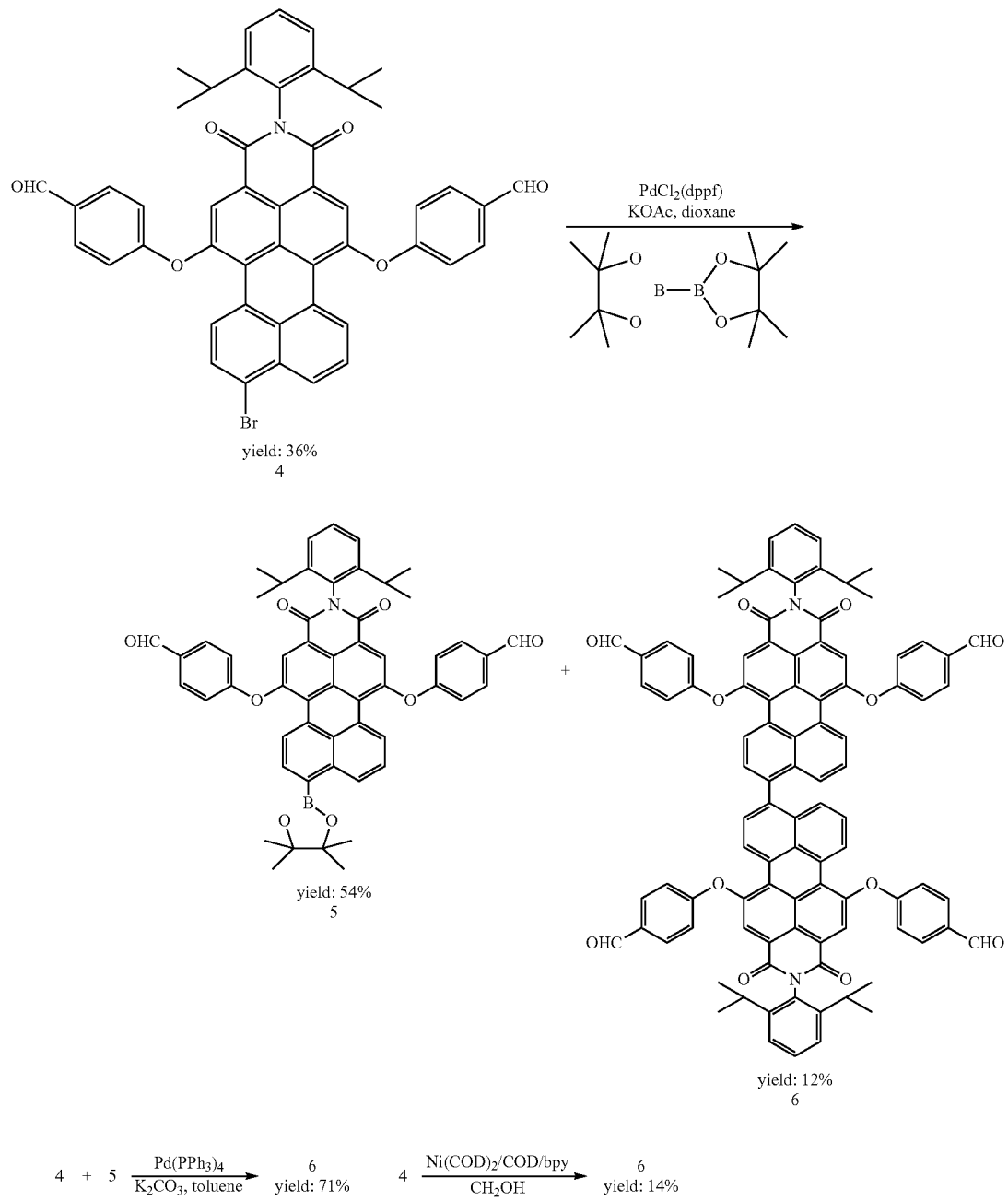

-continued
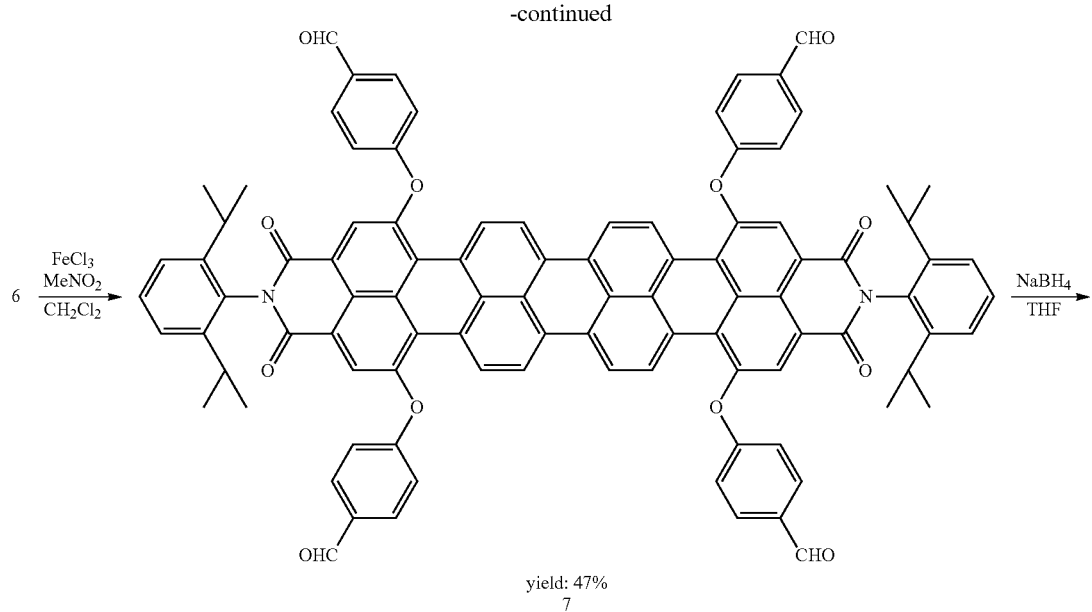
yield: 47%
7
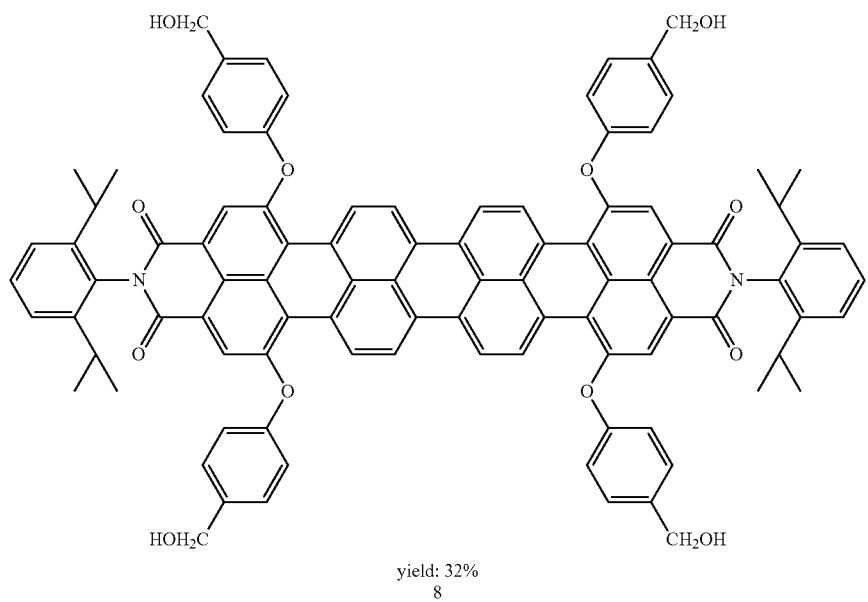
yield: 32%
8
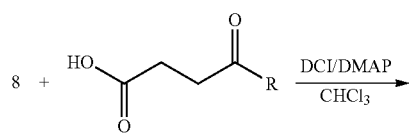
9  R = G1
10 R = G2

-continued
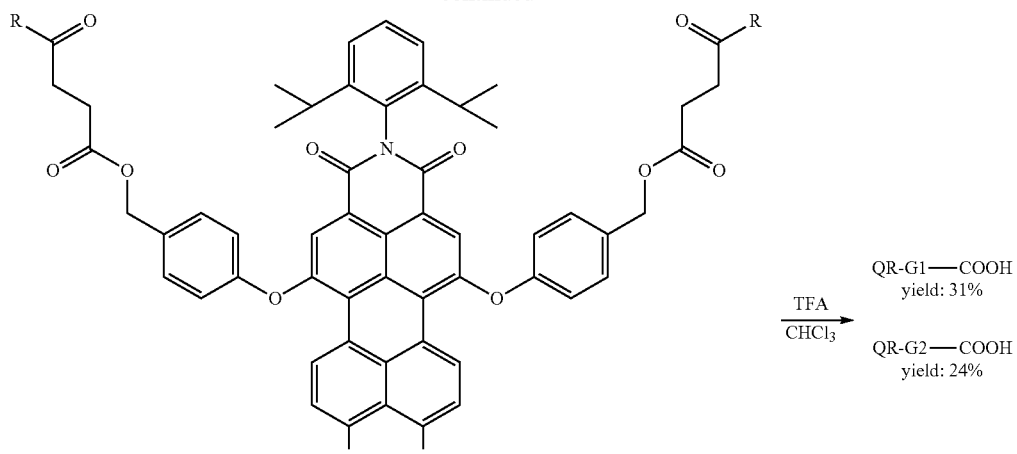
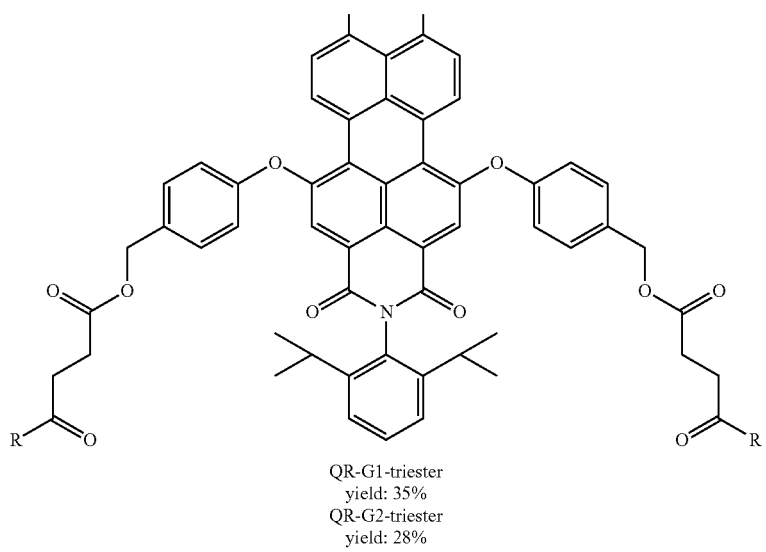
QR-G1-triester
yield: 35%
QR-G2-triester
yield: 28%
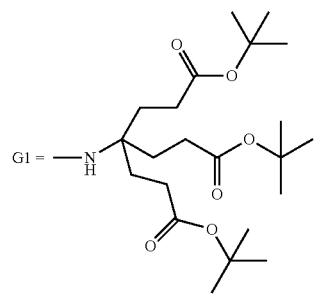

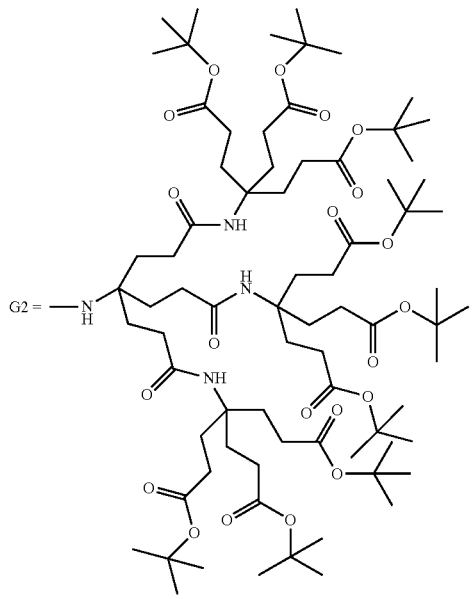

The most challenging step encountered during the synthesis of QR-G1-COOH and QR-G2-COOH was the ring cyclization of biperylene 6. Many quaterrylenes reported were synthesized through a base-assisted cyclodehydrogenation reaction using molten KOH/glucose, tert-BuOK/DBN in diglyme, or $K_2CO_3$ in ethanolamine. However, these reaction systems are not applicable for the synthesis of quaterrylene 7 because of the high reactivity of aldehyde under the harsh basic conditions. Recently, Müllen's group reported milder conditions for the preparation of uaterrylenedicarboximides and rylenediimides by the Lewis acids $FeCl_3/CH_3NO_2$ and $AlCl_3$/chlorobenzene. Although treating 6 with $AlCl_3$/chlorobenzene failed to yield the quaterrylene compound 7, cyclodehydrogenation of 6 with $FeCl_3/CH_3NO_2$ led to the desired product with a moderate yield (47%). The following reduction of aldehyde groups on 7 by $NaBH_4$ yielded benzyl alcohol 8 with a relatively low yield (32%). Coupling quaterrylene 8 with dendrons 9 and 10 provided the dendrimers QR-G1-triester and QR-G2-triester in 35% and 28% yields after purification by column chromatography. Dendrimers QR-G1-triester and QR-G2-triester were highly soluble in organic solvents such as toluene, dichloromethane (DCM), chloroform, ethyl acetate, as well as methanol, and they were characterized by $^1$H NMR, $^{13}$C NMR, and MALDI-TOF mass spectrometry. The next deprotection reaction with TFA/chloroform yielded the target dendrimers QR-G1-COOH and QR-G2-COOH that possess twelve and thirty-six acid groups, respectively. These carboxylic acid groups provide QR-G1-COOH and QR-G2-COOH with high hydrophilicity as sodium salts.

The UV-vis absorption and emission spectra of QR-G1-COOH and QR-G2-COOH in methanol are displayed in FIG. 2 and the spectroscopic data in various solvents are summarized in Table 1 below. QR-G1-COOH has maximum absorption at 771 nm ($\epsilon=1.46\times10^5$ $M^{-5}$ 1 $cm^{-1}$), with a comparable absorption band at 728 nm (E=1.43×10$^5$ $M^{-1}$ $cm^{-1}$). As expected, when excited at 720 nm, QR-G1-COOH showed relatively weak emission at 813 nm in methanol and nearly no fluorescence in water. Similar observations have been reported on extended perylenediimides. The large absorption band at 728 nm and poor fluorescence indicate the presence of strong H-aggregates for QR-G1-COOH, which was further evidenced by the large fluorescence enhancement when the molecule was dissolved in 0.4% wt/wt of pluronic. This fluorescence enhancement in pluronic compared to water can be explained by the disruption of the non-fluorescent dye aggregates by pluronic, which formed micelles with dye monomers inside. The strong absorption in the NIR region and weak emission may render QR-G1-COOH to a promising photoacoustic imaging agent.

TABLE 1

Photophysical properties of QR-G1-COOH and QR-G2-COOH

| | QR-G1-COOH | | | QR-G2-COOH | | |
|---|---|---|---|---|---|---|
| | $\lambda_{obs}$/nm | $\epsilon/10^5$ $M^{-1}$ $cm^{-1}$ | $\lambda_{em}$/nm$^a$ ($\Phi$/%) | $\lambda_{abs}$/nm | $\epsilon/10^5$ $M^{-1}$ $cm^{-1}$ | $\lambda_{em}$/nm$^a$ ($\Phi$/%) |
| Methanol | 771 728 | 1.46 1.43 | 813 | 781 | 1.21 | 815 |
| DMSO | 788 720 | 0.53 0.76 | 816 (0.11) | 788 723 | 1.19 0.55 | 816 (0.32) |
| Water | 739 | 0.74 | — | 743 | 0.56 | — |
| Water, pluronic$^b$ | 782 712 | 1.22 0.57 | 807 | 791 723 | 1.31 0.6 | 809 |

$^a$Fluoresence quantum yield; ICG in methanol was used as standard ($\Phi$ = 7.8%, ref. 6).
$^b$The pluronic concentration is ~0.4 wt %/wt for QR-G1-COOH and ~10 wt %/wt for QR-G2-COOH.

QR-G2-COOH has a similar maximum absorption wavelength (781 nm, E=1.21×10⁵ M⁻¹ cm⁻¹) to QR-G1-COOH, but with a lower absorption shoulder at around 720 nm (FIG. 2). In addition, QR-G2-COOH has significantly higher fluorescence than QR-G1-COOH, with a quantum yield roughly two times higher than that of QR-G1-COOH (Table 1). These data indicate that QR-G2-COOH has less H-aggregates than QR-G1-COOH, and enlargement of the dendrimer size appears to be an effective approach to improve the fluorescence of quaterrylene dendrimers.

To evaluate the photostability of QR-G1-COOH and QR-G2-COOH, the NIR absorbance of these molecules exposed to ambient light was monitored and the results were compared with that of the FDA approved NIR dye, indocyanine green (ICG). As shown in FIG. 3, after being exposed to ambient light for only 2 hours, the absorbance of ICG solution decreased by 48%, whereas solutions of QR-G1-COOH and QR-G2-COOH exhibited no significant absorbance change.

After 3 days of illumination, no significant absorbance from the ICG sample was observed, while QR-G1-COOH and QR-G2-COOH showed an absorbance change of only 1% and 3%, respectively. Even after being exposed to the ambient light for 31 days, QR-G1-COOH and QR-G2-COOH retained strong NIR absorbance of 85% and 77%, respectively. These data demonstrate that QR-G1-COOH and QR-G2-COOH are dramatically more photostable than ICG. The remarkable photostability of these dendrimers provides opportunities in long-term imaging and accurate signal quantification.

Figure 4:
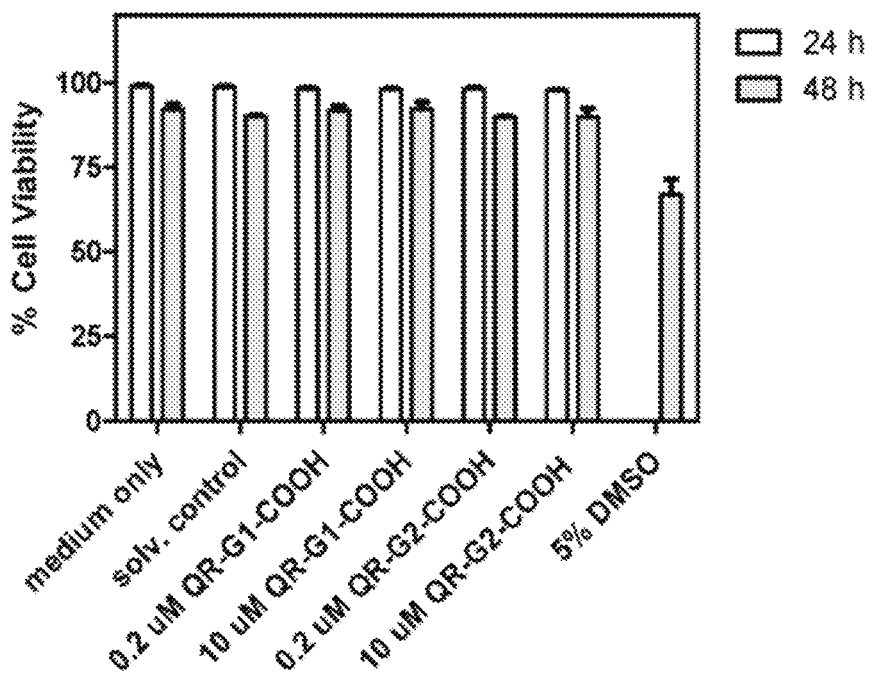
FIG. 4 is a graph showing the results cell viability tests of QR-G1-COOH and QR-G2-COOH on the wt-DBT cell line. Values are presented as mean±standard deviation.

The in vitro cytotoxicity of QR-G1-COOH and QR-G2-COOH against wild-type mouse malignant astrocytoma DBT (wt-DBT) cells was investigated using a hemocytometer-based trypan blue dye exclusion method. FIG. 4 shows the cell viability after incubation with QR-G1-COOH and QR-G2-COOH at concentrations of 2×10⁻⁷ and 1×10⁻⁵ M for 24 and 48 hours. Cell viabilities of more than 97% were observed for both quaterrylene dendrimers at the tested concentrations in 24 h; after 48 h, their cell viabilities were about 90% and the values were comparable to those of the solvent and cell medium control groups, while only 66.9% live cells were found in the positive control group (5% DMSO). The cytotoxicity results indicate that QR-G1-COOH and QR-G2-COOH have low cytotoxicity to DBT cells.

Several embodiments are described below in the following numbered paragraphs:

1. A compound comprising a quaterrylene dye moiety as core, and a dendrimeric shell.

2. A compound comprising four dendronized polyamides covalently attached to a quaterrylene dye.

3. The compound of paragraph 1 comprising at least four dendronized polyamides covalently attached to the quaterrylene dye.

4. The compound of paragraph 3, wherein the dendronized polyamides are covalently attached to at least one quaterrylene dye core moiety.

5. The compound of paragraph 3, wherein four dendronized polyamides are covalently attached to the quaterrylene dye.

6. The compound of any one of paragraphs 1 to 5, wherein the dendrimer shell or dendronized polyamides are functionalized with carboxylate, carboxylic acid or anhydride thereof, hydroxyl, amino, azide, alkynyl, activated alkene, thiol, thioether, thioester, haloacetamide, disulfide, aldehyde, hydrazide, alkoxyamine, hydrozone, thiocyanate, isothiocyanate, cyanate, isocyanate, squarate, or a combination thereof.

7. A compound, or a pharmaceutically acceptable salt or ester thereof, comprising $A(G)_x$, wherein:
   A comprises a quaterrylene dye;
   G comprises at least one functionalized dendrimeric structure; and
   x is 2 to 16.

8. The compound of paragraph 7, wherein the functionalized dendrimeric structure G includes a branched ester, a branched amidoester, a branched alkyl carboxylate or a branched alkyl carboxylic acid structure.

9. The compound of paragraph 7, wherein the dendrimeric structure G includes a structure of:

—OC(O)—X₁—C(O)NH—C(X₂Y)ₐ wherein X₁ and X₂ are each individually an alkanediyl, or X₂ is —X₁—C(O)NH—C(X₂Y)ₐ;
Y is a functional group selected from carboxylic acid or anhydride thereof, carboxylate, hydroxyl, amino, azide, alkynyl, activated alkene, thiol, thioether, thioester, haloacetamide, disulfide, aldehyde, hydrazide, alkoxyamine, hydrozone, thiocyanate, isothiocyanate, cyanate, isocyanate, squarate, or a combination thereof; and
a is 1 to 3

10. The compound of any one of paragraphs 7 to 9, wherein x is 4.

11. The compound of any one of paragraphs 1 to 10, wherein the quaterrylene dye is derived from a 1,6,11,16-tetraaryloxyquaterrylene-3,4:13,14-tetracaroxylic diimide having a structure of:

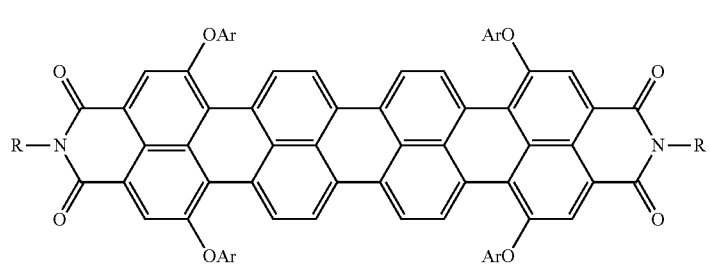

Formula I wherein R is hydrogen; $C_1$-$C_{30}$-alkyl whose carbon chain may be interrupted by one or more of —O—, —S—, —$NR^1$—, —CO— and/or —$SO_2$— and which may be monosubstituted or polysubstituted by cyano, $C_1$-$C_6$-alkoxy or a 5-, 6- or 7-membered heterocyclic radical which is attached via a nitrogen atom and which may contain further heteroatoms and may be aromatic, where $R^1$ is hydrogen or $C_1$-$C_6$-alkyl; $C_5$-$C_8$-cycloalkyl whose carbon skeleton may be interrupted by one or more of —O—, —S— and/or —$NR^1$—; aryl or heteroaryl, which may each be monosubstituted or poly-substituted by $C_1$-$C_{18}$-alkyl, $C_1$-$C_6$-alkoxy, cyano, —$CONHR^2$, —$NHCOR^2$ and/or aryl- or heteroarylazo, which may each be substituted by $C_1$-$C_{10}$-alkyl, $C_1$-$C_6$-alkoxy or halogen, where $R^2$ is hydrogen; $C_1$-$C_{18}$-alkyl; aryloxy, arylthio, heteroaryloxy or heteroarylthio, which may each be substituted by $C_1$-$C_4$-alkyl or $C_1$-$C_4$-alkoxy; and Ar is a substituted aryl group.

12. The compound of any one of paragraphs 1 to 11, wherein the compound includes at least one moiety selected from a therapeutic moiety, a targeting moiety, a signaling moiety, a hydrophilic moiety, or a combination thereof.

13. The compound of paragraph 6 or 9, wherein the compound further comprises at least one moiety selected from a therapeutic moiety, a targeting moiety, a signaling moiety, a hydrophilic moiety, or a combination thereof, wherein the moiety is conjugated to the compound via the functional group.

14. The compound of any one of paragraphs 1 to 13, wherein the compound is biocompatible.

15. The compound of any one of paragraphs 1 to 14, wherein the compound is water soluble.

16. The compound of any one of paragraphs 12 to 15, wherein the therapeutic moiety is an anti-cancer agent.

17. The compound of any one of paragraphs 12 to 16, wherein the targeting moiety is selected from at least one receptor ligand, peptide, protein, antibody, antibody fragment, nucleic acid, or a combination thereof.

18. The compound of any one of paragraphs 12 to 17, wherein the signaling moiety is selected from at least one radioisotope, supermagnetic or paramagnetic metal, fluorophore, microbubble, iodine or a combination thereof.

19. The compound of any one of paragraphs 12 to 18, wherein the hydrophilic moiety is selected from $SO_3^{-2}$, $COO^{-1}$, $PO_4^{-3}$, $(CH_3)_3N^{+1}$, $(CH_3CH_2)_3N^{+1}$, $(HOCH_2CH_2)_3N^{+1}$, methyl pyridine$^{+1}$, polyalkylene oxide, polyglycerol, poly(vinyl alcohol), a mono, oligo or polysaccharide, or a combination thereof.

20. A method of monitoring a therapeutic or diagnostic agent in a subject, comprising administering to the subject a compound of any one of paragraphs 1 to 19; and monitoring the compound within the subject.

21. The method of paragraph 20, wherein the monitoring is selected from optical imaging, positron emission tomography, computed tomography, magnetic resonance imaging, photoacoustic imaging, or ultrasound.

22. The method of paragraph 20 or 21, wherein the monitoring is real-time in vivo monitoring.

23. The method of any one of paragraphs 21 to 22, wherein the therapeutic or diagnostic agent is a therapeutic or targeting moiety coupled to the compound.

24. A method comprising administering to a subject a compound of any one of paragraphs 1 to 19.

25. The method of paragraph 24, wherein the method comprises delivering a therapeutic agent to the subject for treating a disease or condition in the subject, and the therapeutic agent is a therapeutic moiety coupled to the compound.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound comprising a quaterrylene dye moiety as core, and a dendrimeric shell.

2. A compound comprising four dendronized polyamides covalently attached to a quaterrylene dye.

3. The compound of claim 1 comprising at least four dendronized polyamides covalently attached to the quaterrylene dye.

4. The compound of claim 3, wherein the dendronized polyamides are covalently attached to at least one quaterrylene dye core moiety.

5. The compound of claim 3, wherein four dendronized polyamides are covalently attached to the quaterrylene dye.

6. The compound of claim 1, wherein the dendrimer shell is functionalized with carboxylate, carboxylic acid or anhydride thereof, hydroxyl, amino, azide, alkynyl, activated alkene, thiol, thioether, thioester, haloacetamide, disulfide, aldehyde, hydrazide, alkoxyamine, hydrozone, thiocyanate, isothiocyanate, cyanate, isocyanate, squarate, or a combination thereof.

7. A compound, or a pharmaceutically acceptable salt or ester thereof, comprising $A(G)_x$, wherein:

A comprises a quaterrylene dye;

G comprises at least one functionalized dendrimeric structure; and x is 2 to 16.

8. The compound of claim 7, wherein the functionalized dendrimeric structure G includes a branched ester, a branched amidoester, a branched alkyl carboxylate or a branched alkyl carboxylic acid structure.

9. The compound of claim 7, wherein the dendrimeric structure G includes a structure of:

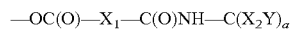

wherein $X_1$ and $X_2$ are each individually an alkanediyl, or $X_2$ is —$X_1$—C(O)NH—$C(X_2Y)_a$;

Y is a functional group selected from carboxylic acid or anhydride thereof, carboxylate, hydroxyl, amino, azide, alkynyl, activated alkene, thiol, thioether, thioester, haloacetamide, disulfide, aldehyde, hydrazide, alkoxyamine, hydrozone, thiocyanate, isothiocyanate, cyanate, isocyanate, squarate, or a combination thereof; and a is 1 to 3.

10. The compound of claim 7, wherein x is 4.

11. The compound of claim 1, wherein the quaterrylene dye is derived from a 1,6,11,16-tetraaryloxyquaterrylene-3,4:13,14-tetracarboxylic diimide having a structure of:

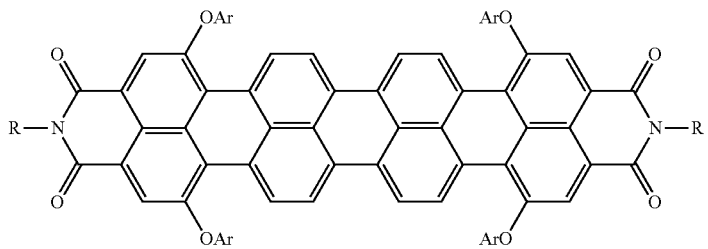

Formula I wherein R is hydrogen; $C_1$-$C_{30}$-alkyl whose carbon chain may be interrupted by one or more of —O—, —S—, —$NR^1$—, —CO— and/or —$SO_2$— and which may be monosubstituted or polysubstituted by cyano, $C_1$-$C_6$-alkoxy or a 5-, 6- or 7-membered heterocyclic radical which is attached via a nitrogen atom and which may contain further heteroatoms and may be aromatic, where $R^1$ is hydrogen or $C_1$-$C_6$-alkyl;

$C_5$-$C_8$-cycloalkyl whose carbon skeleton may be interrupted by one or more of —O—, —S— and/or —$NR^1$—; aryl or heteroaryl, which may each be mono-substituted or poly-substituted by $C_1$-$C_{18}$-alkyl, $C_1$-$C_6$-alkoxy, cyano, —$CONHR^2$, —$NHCOR^2$ and/or aryl- or heteroaryl-azo, which may each be substituted by $C_1$-$C_{10}$-alkyl, $C_1$-$C_6$-alkoxy or halogen, where $R_2$ is hydrogen; $C_1$-$C_{18}$-alkyl; aryloxy, arylthio, heteroaryloxy or heteroarylthio, which may each be substituted by $C_1$-$C_4$-alkyl or $C_1$-$C_4$-alkoxy; and Ar is a substituted aryl group.

12. The compound of claim 1, wherein the compound includes at least one moiety selected from a therapeutic moiety, a targeting moiety, a signaling moiety, a hydrophilic moiety, or a combination thereof.

13. The compound of claim 9, wherein the compound further comprises at least one moiety selected from a therapeutic moiety, a targeting moiety, a signaling moiety, a hydrophilic moiety, or a combination thereof, wherein the moiety is conjugated to the compound via the functional group.

14. The compound of claim 1, wherein the compound is biocompatible.

15. The compound of claim 1, wherein the compound is water soluble.

16. The compound of claim 12, wherein the therapeutic moiety is an anti-cancer agent.

17. The compound of claim 12, wherein the targeting moiety is selected from at least one receptor ligand, peptide, protein, antibody, antibody fragment, nucleic acid, or a combination thereof.

18. The compound of claim 12, wherein the signaling moiety is selected from at least one radioisotope, supermagnetic or paramagnetic metal, fluorophore, microbubble, iodine or a combination thereof.

19. The compound of claim 12, wherein the hydrophilic moiety is selected from $SO_3^{-2}$, $COO^{-1}$, $PO_4^{-3}$, $(CH_3)_3N^{+1}$, $(CH_3CH_2)_3N^{+1}$, $(HOCH_2CH_2)_3N^{+1}$, methyl pyridine$^{+1}$, polyalkylene oxide, polyglycerol, poly(vinyl alcohol), a mono, oligo or polysaccharide, or a combination thereof.

20. A method of monitoring a therapeutic or diagnostic agent in a subject, comprising administering to the subject a compound of claim 1; and monitoring the compound within the subject.

21. The method of claim 20, wherein the monitoring is selected from optical imaging, positron emission tomography, computed tomography, magnetic resonance imaging, photoacoustic imaging, or ultrasound.

22. The method of claim 20, wherein the monitoring is real-time in vivo monitoring.

23. The method of claim 21, wherein the therapeutic or diagnostic agent is a therapeutic or targeting moiety coupled to the compound.

24. A method comprising administering to a subject a compound of claim 1.

25. The method of claim 24, wherein the method comprises delivering a therapeutic agent to the subject for treating a disease or condition in the subject, and the therapeutic agent is a therapeutic moiety coupled to the compound.

26. The compound of claim 7, wherein the quaterrylene dye is derived from a 1,6,11,16-tetraaryloxyquaterrylene-3,4:13,14-tetracarboxylic diimide having a structure of:

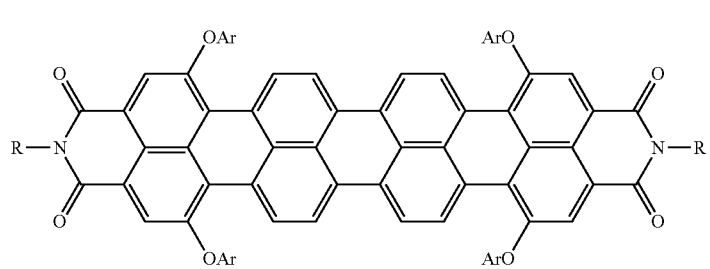

Formula I wherein R is hydrogen; $C_1$-$C_{30}$-alkyl whose carbon chain may be interrupted by one or more of —O—, —S—, —$NR^1$—, —CO— and/or —$SO_2$— and which may be monosubstituted or polysubstituted by cyano, $C_1$-$C_6$-alkoxy or a 5-, 6- or 7-membered heterocyclic radical which is attached via a nitrogen atom and which may contain further heteroatoms and may be aromatic, where $R^1$ is hydrogen or $C_1$-$C_6$-alkyl;

$C_5$-$C_8$-cycloalkyl whose carbon skeleton may be interrupted by one or more of —O—, —S— and/or —$NR^1$—; aryl or heteroaryl, which may each be monosubstituted or poly-substituted by $C_1$-$C_{18}$-alkyl, $C_1$-$C_6$-alkoxy, cyano, —$CONHR^2$, —$NHCOR^2$ and/or aryl- or heteroaryl-azo, which may each be substituted by $C_1$-$C_{10}$-alkyl, $C_1$-$C_6$-alkoxy or halogen, where $R_2$ is hydrogen; $C_1$-$C_{18}$-alkyl; aryloxy, arylthio, heteroaryloxy or heteroarylthio, which may each be substituted by $C_1$-$C_4$-alkyl or $C_1$-$C_4$-alkoxy; and Ar is a substituted aryl group.

\* \* \* \* \*